US011066346B2

(12) United States Patent
Fritz et al.

(10) Patent No.: US 11,066,346 B2
(45) Date of Patent: Jul. 20, 2021

(54) METHOD AND SYSTEM FOR OBTAINING ONE OR MORE OLEFINS

(71) Applicant: LINDE AKTIENGESELLSCHAFT, München (DE)

(72) Inventors: Helmut Fritz, Munich (DE); Christian Ernst, Ottobrunn (DE); Tobias Sinn, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 114 days.

(21) Appl. No.: 16/603,480

(22) PCT Filed: Apr. 6, 2018

(86) PCT No.: PCT/EP2018/058903
§ 371 (c)(1),
(2) Date: Oct. 7, 2019

(87) PCT Pub. No.: WO2018/185310
PCT Pub. Date: Oct. 11, 2018

(65) Prior Publication Data
US 2021/0130264 A1 May 6, 2021

(30) Foreign Application Priority Data
Apr. 7, 2017 (EP) .................................. 17165594

(51) Int. Cl.
*C07C 7/00* (2006.01)
*B01D 3/00* (2006.01)
(Continued)

(52) U.S. Cl.
CPC .............. *C07C 7/005* (2013.01); *B01D 3/007* (2013.01); *B01D 3/141* (2013.01); *B01D 3/148* (2013.01);
(Continued)

(58) Field of Classification Search
CPC ........... C07C 11/04; C07C 2/84; C07C 7/005; C07C 7/04; B01D 3/007; B01D 3/141; B01D 3/143; B01D 3/148; B01D 3/14
See application file for complete search history.

(56) References Cited

U.S. PATENT DOCUMENTS

| 4,157,904 A | 6/1979 | Campbell et al. |
| 2017/0107462 A1* | 4/2017 | Frankenbach ........ D06M 23/02 |

FOREIGN PATENT DOCUMENTS

| DE | 3814187 A1 | 11/1989 |
| EP | 0316768 A2 | 5/1989 |
| EP | 1818634 A2 | 8/2007 |

OTHER PUBLICATIONS

PCT/EP2018/058903 International Search Report dated Jun. 18, 2018, 2 pages.
(Continued)

*Primary Examiner* — Sharon Pregler
(74) *Attorney, Agent, or Firm* — Lathrop GPM LLP

(57) ABSTRACT

The invention relates to a method (100, 200) of obtaining one or more olefins, in which, using an oxidative coupling of methane (10), a gas mixture comprising hydrogen, methane, carbon monoxide and higher-boiling hydrocarbons than methane is formed and is subjected to a low-temperature separation (1-5), characterized in that the low-temperature separation (1-5) is conducted using a rectification column (2) having a first separation region (21), a second separation region (22) arranged above the first separation region (21), and a condenser-evaporator (23), wherein the gas mixture is cooled, fed at least partly as first separation feed into the first separation region (21) and subjected to a first rectification in the first separation region (21) to form a first tops gas and a first bottoms liquid, wherein, using a first proportion of the first tops gas in the condenser-evaporator (23), a condensate which is recycled to the first separation region and, using a
(Continued)

second proportion of the tops gas, a second separation feed which is fed into the second separation region (22) are formed, and wherein the second separation feed is subjected to a second rectification in the second separation region to form a second tops gas and a second bottoms liquid.

20 Claims, 2 Drawing Sheets

(51) Int. Cl.
*B01D 3/14* (2006.01)
*B01D 5/00* (2006.01)
*C07C 2/84* (2006.01)
*C07C 7/04* (2006.01)
*F25J 3/02* (2006.01)

(52) U.S. Cl.
CPC .............. *B01D 5/0003* (2013.01); *C07C 2/84* (2013.01); *C07C 7/04* (2013.01); *F25J 3/0219* (2013.01); *F25J 3/0233* (2013.01); *F25J 3/0238* (2013.01); *F25J 2200/06* (2013.01); *F25J 2200/72* (2013.01); *F25J 2210/12* (2013.01); *F25J 2270/04* (2013.01); *F25J 2290/12* (2013.01); *F25J 2290/40* (2013.01)

(56) References Cited

OTHER PUBLICATIONS

PCT/EP2018/058903 International Preliminary Report on Patentability (Chapter II) dated Mar. 7, 2019, 6 pages.

* cited by examiner

METHOD AND SYSTEM FOR OBTAINING ONE OR MORE OLEFINS

CROSS-REFERENCE TO RELATED APPLICATIONS

This application is a 35 U.S.C. § 371 national phase application of PCT/EP2018/058903, filed Apr. 6, 2018. PCT/EP2018/058903 claims the benefit of priority from European Patent Application No. 17165594.7, filed Apr. 7, 2017, the contents of which are hereby incorporated by reference in their entirety.

FIELD

The invention relates to a method of obtaining one or more olefins and to a corresponding plant according to the preamble of the respective independent claims.

PRIOR ART

The oxidative coupling of methane is described in the literature, for example in J. D. Idol et al., "Natural Gas", in: J. A. Kent (ed.), "Handbook of Industrial Chemistry and Biotechnology", volume 2, 12th edition, Springer, New York 2012.

According to the current state of knowledge, the oxidative coupling of methane comprises a catalysed gas phase reaction of methane with oxygen, in which one hydrogen atom is split off from each of two methane molecules. The resultant methyl radicals react at first to form an ethane molecule. The reaction also forms a water molecule. Given suitable ratios of methane to oxygen, suitable reaction temperatures and the choice of suitable catalysis conditions, there is subsequently oxydehydrogenation of the ethane to give ethylene, a target compound in the oxidative coupling of methane. A further water molecule is formed here. The oxygen used is typically fully converted in the reactions mentioned.

The reaction conditions in the oxidative coupling of methane conventionally include a temperature of 500 to 900° C., a pressure of 5 to 10 bar and high space velocities. More recent developments are in the direction of the use of lower temperatures in particular. The reaction can be effected under homogeneous and heterogeneous catalysis in a fixed bed or a fluidized bed. In the oxidative coupling of methane, it is also possible for higher hydrocarbons having up to six or eight carbon atoms to be formed, but the emphasis is on ethane/ethylene and, as the case may be, also propane/propylene.

Especially because of the high binding energy between carbon and hydrogen in the methane molecule, the yields in the oxidative coupling of methane are comparatively low. Typically, not more than 10% to 15% of the methane used is converted. Moreover, the comparatively harsh reaction conditions and temperatures required for scission of these bonds also promote the further oxidation of the methyl radicals and other intermediates to give carbon monoxide and carbon dioxide.

Although the low yields and the formation of carbon monoxide and carbon dioxide can be partly counteracted by the choice of optimized catalysts and of adjusted reaction conditions, a gas mixture formed in the oxidative coupling of methane, as well as the target compounds such as ethylene and possibly propylene, comprises predominantly unconverted methane, and also carbon dioxide, carbon monoxide and water. As a result of noncatalytic cleavage reactions that may take place, it is also possible for considerable amounts of hydrogen to be present. A gas mixture of this kind, in the terminology being used here, is also referred to as "product mixture" of the oxidative coupling of methane, even though it does not comprise the desired products to a predominant degree, but also comprises the unconverted methane reactant and the by-products just elucidated.

In the oxidative coupling of methane, it is possible to use reactors in which a catalytic zone is followed downstream by a noncatalytic zone. The gas mixture flowing out of the catalytic zone is transferred into the noncatalytic zone, where it is at first still at the comparatively high temperatures that are used in the catalytic zone. Especially by virtue of the presence of the water which is formed in the oxidative coupling of methane, the reaction conditions here are similar to those in conventional steamcracking methods. Therefore, it is possible here for ethane and higher paraffins to be converted to olefins. It is also possible for further paraffins to be fed into the noncatalytic zone, such that the residual heat from the oxidative coupling of methane can be exploited in a particularly advantageous manner. Controlled steamcracking of this kind in a noncatalytic zone connected downstream of the catalytic zone is also referred to as "post-bed cracking". This is also referred to hereinafter by the term "postcatalytic steamcracking".

With regard to the reaction conditions that exist in steamcracking, reference is likewise made to specialist literature such as the article "Ethylene" in Ullmann's Encyclopedia of Industrial Chemistry, Online Edition, 15 Apr. 2007, DOI 10.1002/14356007.a10_045.pub2. Steamcracking is used, for example, to obtain short-chain olefins such as ethylene and propylene, diolefins such as butadiene or aromatics, but is not limited thereto.

Product mixtures that are formed using a method of oxidative coupling of methane, for the reasons elucidated above, especially contain large amounts of methane, which should advantageously be removed and recycled into the oxidative coupling. The fractional processing of a corresponding product mixture, owing to the high methane content coupled with the comparatively low content of target products, is found to be extremely complex.

The fractional processing of the product mixture conventionally comprises cooling to ambient temperature. This condenses out the predominant portion of the water present in the product mixture. The cooling is effected at the pressure at which the product mixture is present downstream of the oxidative coupling of methane, i.e. typically 5 to 10 bar, for example 7 to 8 bar. This is followed by a compression and subsequently a removal of the carbon dioxide from the product mixture, for example using an amine and/or alkali scrub. Residual water is subsequently removed typically by adsorptive means, for example using molecular sieve adsorbers.

A gas mixture obtained from the product mixture by appropriate processing is sent to a low-temperature separation in which methane and lower-boiling components than methane, i.e. carbon monoxide and hydrogen in particular, if present, are at least predominantly removed. The residual hydrocarbon mixture comprises predominantly or exclusively ethylene and higher-boiling compounds than ethylene, if present in the product mixture.

Methods of removing methane and lower-boiling compounds from different hydrocarbon mixtures, for example from natural gas or from gas mixtures that have been obtained using steamcracking methods, are known in principle from the prior art. However, these methods can have drawbacks in the fractional processing of gas mixtures that have been obtained using the oxidative coupling of methane. For example, Ortloff's Recycle Split Vapor (RSV) method which is used for natural gas, as disclosed in U.S. Pat. No. 4,157,904 A and elucidated in detail in H.-W. Haring (ed.), Industrial Gases Processing, Wiley-VCH, 2006, section 7.6.2, "Separation of Liquefied Petroleum Gas", is unsuitable for the separation of a gas mixture which has been obtained using the oxidative coupling of methane, since the required purities cannot be achieved easily owing to the differing composition.

The aim of the present invention is therefore especially to improve the separation of methane and lower-boiling compounds from a gas mixture that has been obtained using the oxidative coupling of methane by comparison with the prior art, and to optimize it in terms of energy and/or apparatus.

DISCLOSURE OF THE INVENTION

Against this background, the present invention proposes a method of obtaining one or more olefins and a corresponding plant according to the preamble of the respective independent claims. Configurations are each subject matter of the dependent claims and of the description which follows.

Before elucidating the features and advantages of the present invention, a few basic principles and the terms used will be elucidated.

Where it is said hereinafter that a gas mixture is formed "using a method of oxidative coupling of methane", this shall be understood to mean that the formation of the product mixture involves a method that comprises the reactions elucidated above, especially the formation of methyl radicals, the coupling thereof to form ethane and the subsequent oxydehydrogenation. In addition, however, further methods or method steps may be encompassed, especially the above-elucidated postcatalytic steamcracking. Further feeds that have been at least partly converted to products present in the gas mixture may be fed to this or these further method(s) or method step(s). In other words, formation of the gas mixture "using" the method of oxidative coupling of methane need not solely involve the oxidative coupling of methane.

In a corresponding manner, a "reactor set up for oxidative coupling of methane" shall be understood hereinafter to mean a reactor having, at least in one reactor zone, a catalyst suitable for the oxidative coupling of methane. At least in this reactor zone, by suitable means, for example by means of burners and upstream compressors, temperature and pressure conditions that lead to oxidative coupling of methane under the influence of the catalyst can be created, as elucidated above. A corresponding reactor may, as well as the reactor zone elucidated, have further reactor zones, especially a noncatalytic zone arranged downstream of the catalytic zone, which is used for the postcatalytic steamcracking elucidated, and into which further hydrocarbons can be fed.

In the context of the present linguistic usage, liquid and gaseous mixtures may be rich or poor in one or more components, wherein "rich" may represent a content of not less than 50%, 75%, 90%, 95%, 99%, 99.5%, 99.9% or 99.99% and "poor" may represent a content of not more than 50%, 25%, 10%, 5%, 1%, 0.1% or 0.01% on a molar, weight or volume basis. The expression "predominantly" may correspond to the definition of "rich".

For characterization of pressures and temperatures, the present application uses the terms "pressure level" and "temperature level", which is intended to express the fact that corresponding pressures and temperatures in a corresponding plant need not be used in the form of exact pressure and temperature values in order to implement the concept of the invention. However, pressures and temperatures of this kind typically vary within particular ranges, the maximum and minimum values of which differ, for example, by not more than 1%, 5%, 10%, 20% or even 50%.

It is possible here for corresponding pressure levels and temperature levels to lie in disjoint ranges or in overlapping ranges. In particular, pressure levels for example include unavoidable or expected pressure losses, for example owing to cooling effects. The same holds for temperature levels. The pressure levels indicated here in bar are each absolute pressures.

A "rectification column" in the context of the present linguistic usage is a separation unit set up for at least partial fractionation of a substance mixture fed in in gaseous or liquid form or in the form of a biphasic mixture having liquid and gaseous components, possibly even in the supercritical state, by rectification, i.e. to respectively produce pure substances or at least substance mixtures of different composition from the substance mixture.

Rectification columns typically take the form of cylindrical metal vessels equipped with internals, for example sieve trays or ordered or unordered packings. As well as the regions intended for the actual separation, which are also referred to hereinafter as "separation regions", rectification columns may also have regions intended for other purposes, for example condensation spaces that are set up merely for phase separation of biphasic mixtures, and in this way essentially replace a corresponding external vessel.

A rectification column comprises a reboiler. This is a device having a heat exchanger which is heated and which has been set up to heat a liquid fraction that accumulates in the bottom of the rectification column, also referred to as bottoms liquid. By means of a reboiler, a portion of the bottom product is continuously evaporated and fed back in gaseous form in the separation region.

By contrast with a rectification column, an "absorption column" does not have a reboiler, but has a means of feeding in an absorption liquid at the top end. Absorption columns are used for absorption in phase countercurrent and are therefore also referred to as countercurrent columns. In the case of absorption in phase countercurrent, the releasing gas phase flows upward through the absorption column. The absorbing absorption liquid flows counter to the gas phase, being applied at the top and drawn off at the bottom. Internals are likewise typically provided in an absorption column, which ensure stepwise or constant phase contact.

In the context of the present linguistic usage, an "absorbate" is understood to mean the laden absorption liquid obtained in the bottom of an absorption column. A corresponding absorbate contains the components of the absorption liquid that reach the bottom of the absorption column in liquid form and the components that have been absorbed from the gas phase. The unabsorbed components are not transferred to the absorbate. The definition used corresponds to that in standard textbooks, for example chapter 10.1, "Absorption", in: B. Lohrengel, "Einführung in die thermischen Trennverfahren: Trennung von Gas-, Dampf- and Flüssigkeitsgemischen" [Introduction to Thermal Separation Processes: Separation of Gas, Vapour and Liquid Mixtures], 2nd edition, De Gruyter, Oldenbourg, Berlin 2012.

A "condenser-evaporator" has a liquefaction space and an evaporation space. The evaporation and liquefaction spaces are typically formed by groups of passages (liquefaction or evaporation passages) of a heat exchanger in fluid connection with one another. The condensation of a first fluid stream is conducted in the liquefaction space, and the evaporation of a second fluid stream in the evaporation space. The two fluid streams are in indirect heat exchange. A condenser-evaporator may be integrated into a rectification column. Alternatively, condenser-evaporators may also be arranged outside a corresponding rectification column. In a corresponding condenser-evaporator of a rectification column, fluid ascending in gaseous form from a separation region, i.e. what is called the "tops gas", is at least partly condensed and can be recycled to the separation region as liquid reflux. A corresponding condenser-evaporator is cooled with a fluid that enables the at least partial condensation of the tops gas under the prevailing pressure conditions.

Advantages of the Invention

The present invention relates to the separation of a gas mixture which is provided using the oxidative coupling of methane, and which includes methane, lower-boiling components than methane and higher-boiling hydrocarbons than methane. This gas mixture can especially be formed from a product mixture from an oxidative coupling of methane, in that it is compressed and then at least for the most part freed of water and carbon dioxide. As mentioned, formation of the product mixture may also involve further methods or method steps such as postcatalytic steamcracking.

As is known in this respect, a gas mixture of this kind may be separated in a rectification column to which a reflux which is formed by partial condensation of tops gas from the rectification column as condensate is applied. The tops gas comprises predominantly or exclusively methane and lower-boiling compounds than methane. A further portion of the tops gas, especially the portion thereof that remains in gaseous form in the partial condensation, can be fed to one or more further separation units downstream of the rectification column, for example in order to remove methane which is to be recycled into the oxidative coupling of methane.

The present invention is based on the finding that it is particularly advantageous when a corresponding gas mixture is subjected to a low-temperature rectification in a rectification column having two or more separation regions, wherein the separation regions have fluid connection to one another. An intermediate condensation is effected here using one or more condenser-evaporators arranged between the separation regions for processing purposes.

A rectification of this kind, especially by comparison with the conventional methods mentioned at the outset, can be effected at much lower pressures. What is meant by an arrangement of the condenser-evaporator(s) "between" corresponding separation regions "for processing purposes" is thus not, or at least not necessarily, a spatial interconnection in the sense that the respective parts are arranged one on top of another in geodetic terms and the respective condenser-evaporator is arranged above the first and below the second separation region in geodetic terms. What is meant thereby is more that a top product from a separation region can be condensed below the uppermost separation region, which is thus arranged in an intermediate region of the overall rectification in the overall column.

In the case of low-temperature rectification, the rectification column is operated in conventional methods with a reflux which is formed by condensing a portion of the tops gas from the rectification column. Pure methane at −97° C. has a boiling pressure of about 29 bar. If hydrogen is also present as well as methane in a corresponding gas mixture, for example in a content of 5 to 10 mole percent in the gas mixture outlined, there is a distinct increase in the boiling pressure.

Therefore, in order to enable the condensation of the hydrogenous tops gas, it would be necessary in conventional methods either to increase the rectification pressure or to resort to lower-boiling coolants such as methane. Condensation of the tops gas at a rectification pressure of below 30 bar and use of ethylene as coolant is not possible because ethylene does not cool down below about −102° C. under customary conditions, i.e. as "low-pressure ethylene" at a pressure of just above 1 bar, and hence a gas mixture can be cooled down by means of ethylene only to about −100° C.

The high rectification pressures in the first alternative firstly entail rectification columns that are costly because they have to be rated for correspondingly high pressure. Secondly, rectification at correspondingly high pressures is much more complex because there is a reduction in the density differential between gas and liquid. The relative volatilities approach one another at correspondingly high pressures, and the separation becomes more thermodynamically difficult. A corresponding rectification column therefore also has to have a much greater volume. As well as the compressive strength required, this likewise increases the build costs for a corresponding rectification column. In the case of relatively large volume flows to be processed, the use of two or more rectification columns arranged in parallel is required in order not to meet constructibility limits. This further increases the expense of corresponding plants.

Use of large amounts of externally provided coolant having a lower boiling point than ethylene according to the second alternative is likewise generally undesirable owing to the additional complexity involved in the provision thereof. However, one means of achieving lower temperatures than with ethylene is, for example, to partly expand the tops gas from the low-temperature rectification, which of course comprises predominantly or exclusively methane and hydrogen. This is especially true when the tops gas can be utilized at a lower pressure level than the pressure level for the low-temperature rectification. However, the cooling energy that can be formed in this way is typically insufficient to condense the tops gas in the desired volume.

However, the present invention cannot just be used in cases where appropriate proportions of tops gas from the low-temperature rectification are expanded for generation of low temperatures and the cooling energy released is insufficient. Rather than tops gas, it is also possible, for example, to use methane from a methane cooling circuit or a correspondingly low-boiling mixed coolant. A corresponding cooling circuit can then have deliberately smaller dimensions through the use of the present invention in order to save energy and reduce the implementation costs. In this case too, cooling energy from the expanded methane is insufficient for condensation.

According to the present invention, therefore, ethylene is used as coolant in addition to the insufficient lower-boiling coolant than ethylene at the top of the rectification column, for example the expanded tops gas. However, it is not used entirely at the top of the rectification column, but instead at one or more positions beneath at which the ethylene temperature of about −102° C. is sufficient to bring about condensation and hence generate a reflux.

As is well known, a temperature profile that runs from the bottom upward in the direction of lower temperatures forms in a rectification column owing to the heating in the bottom and the cooling at the top. In a rectification column under consideration in the present context, the temperature in the bottom may, for example, be about 0° C. and the temperature at the top below −100° C. Therefore, no point exists at which condensation is possible even with ethylene at about −102° C.

The point at which condensation is effected by means of ethylene cannot be lowered arbitrarily because a sufficient number of plates still has to be present below this and above the feed point for the gas mixture to be separated into the rectification column, in order to be able to scrub ethylene sufficiently out of the gas mixture. The number of plates cannot be increased arbitrarily in a given space because a minimum reflux ratio has to be maintained.

Therefore, the position or positions at which one or more condensations of this kind are conducted has/have to be matched to the respective column dimensions. Since the person skilled in the art is aware, for example, of the temperature profile within a rectification column and the minimum number of plates required, or he is able to ascertain corresponding parameters by simulation, for example, he will be able to select this position or these positions without difficulty. The appropriate dimensions of the column sections and hence also the appropriate position of the intermediate condenser-evaporator(s) can therefore be determined by routine activity for a person skilled in the art.

Since the lowest temperatures are typically achieved at the top in a rectification column, the arrangement of a corresponding condenser-evaporator which is operated, for example, with ethylene coolant or a corresponding cryogenic fluid results in a much greater temperature differential relative to the column temperature at that point in an intermediate region of rectification than in the uppermost region of the overall rectification column. Even though hydrogen is present, the rectification can therefore be effected at lower pressure. Because a corresponding condenser-evaporator, in the context of the present invention, is provided between two separation regions for processing purposes, a preliminary separation can be undertaken in a first separation region below the condenser-evaporator into which the separation feed is also fed, this preliminary separation consisting essentially in a depletion of a portion of the higher-boiling hydrocarbons than methane in the gas mixture. In a second separation region above the condenser-evaporator in which there are lower separation temperatures, it is therefore necessary to separate only a smaller fluid volume in the form of these hydrocarbons from the lighter components. There is therefore a fall in the demand for coolant.

Overall, the present invention proposes a method of obtaining one or more olefins, in which, using an oxidative coupling of methane, a gas mixture comprising hydrogen, methane, carbon monoxide and higher-boiling hydrocarbons than methane is formed and is subjected to a low-temperature separation.

According to the invention, the low-temperature separation is conducted using a rectification column having a first separation region, a second separation region arranged above the first separation region, and a condenser-evaporator which is especially arranged between the first separation region and the second separation region for processing purposes in the sense elucidated above. It should be pointed out that, as already mentioned, in the context of the present invention, it is also possible for multiple condenser-evaporators and in that case also additional separation regions to be provided. The present invention is thus not restricted to the use of just one condenser-evaporator and two separation regions.

In the context of the present invention, the gas mixture is cooled, fed at least partly as first separation feed into the first separation region and subjected to a first rectification in the first separation region to form a first tops gas and a first bottoms liquid. This first rectification is the "preliminary separation" already mentioned above, using said condenser-evaporator as intermediate condenser. This condenser-evaporator can be operated at a sufficiently low temperature level with, as mentioned, ethylene coolant or a corresponding fluid, as will also be elucidated in detail hereinafter. If a corresponding condenser-evaporator, for processing purposes, is arranged above the first separation region, but not above the rectification column used overall, i.e. all separation regions or a single separation region, the result of this, as mentioned, is a greater temperature difference from the separation temperature at the point in the rectification column at which the condenser-evaporator is arranged compared to the temperature difference at the top of the rectification column.

In the context of the present invention, using a first proportion of the first tops gas in the condenser-evaporator, a condensate which is recycled to the first separation region and, using a second proportion of the tops gas, a second separation feed which is fed into the second separation region are formed. The preliminarily separated gas mixture is thus sent to a further separation in the second, upper separation region. The second separation feed is subjected here to a second rectification in the second separation region to form a second tops gas and a second bottoms liquid. This second rectification, as is customary in a rectification, is likewise effected using a liquid reflux, the provision of which is elucidated in detail below. A liquid is especially recycled from a lower region of the second separation region to the first separation region. As mentioned, the volumes to be separated, by virtue of the preliminary separation that has already been effected in the first separation region, are much smaller in the second separation region than in the method according to the prior art. Overall, a corresponding rectification column can therefore be operated at much lower pressures than used in the prior art.

More particularly, in the context of the present invention, the first separation region and the second separation region can be arranged within a common outer shell of a corresponding rectification column. In this way, it is possible to create an integrated unit which especially offers insulation advantages, for example may be disposed in a common coldbox. The condenser-evaporator may be arranged, in terms of construction, between or else at the top of a corresponding rectification column. Since the operating pressure of the separation regions, however, is typically higher than that of the condenser-evaporator, it is preferably arranged outside a common (compressed) outer shell that optionally surrounds the first and second separation regions.

As well as the separation regions mentioned and the condenser-evaporator, a rectification column as usable in the context of the present invention especially also encompasses empty spaces, which are also referred to here as "condensation spaces", and which are set up to be charged with fluid which separates into a gas phase and a liquid phase in corresponding empty spaces. Corresponding empty spaces thus serve for phase separation in accordance with conventional separation vessels. Corresponding empty spaces can especially be separated from the separating regions by liquid barrier plates. A liquid phase that separates out in a corresponding empty space can flow away via an overflow to a separation region beneath.

More particularly, in the context of the present invention, the separation regions within the rectification column are separated from one another by a liquid- and gas-impermeable dividing wall, i.e. exchange of gas and liquid between the separation regions is effected solely through conduits specifically designed for the purpose and can therefore be conducted in a controlled manner.

In the context of the present invention, the cooling of the gas mixture prior to the at least partial feeding thereof as first separation feed into the first separation region is effected to a temperature level of −70 to −95° C. For this cooling, it is possible to use a heat exchanger also elucidated in detail below, which can be cooled with streams formed in the rectification.

Advantageously, a pressure level at which the rectification column is operated is 24 to 36 bar. The separation regions may be operated at slightly different pressures, by means of which it can be ensured that fluids are transferred from the first separation region to the second separation region in the desired manner and especially without additional pumps.

Advantageously, using a first proportion of the second tops gas, i.e. of the corresponding separation product from the second, upper separation region, a condensate which is recycled to the first separation region is formed, wherein a second proportion of the second tops gas is expanded to a lower pressure level and then subjected to a heat exchange with the first proportion of the second tops gas. In this way, condensation of the tops gas from the second, upper separation region can be conducted. The expansion of the second proportion of the second top product provides cooling energy at a temperature level of typical "C1 chill". This is suitable for at least partly condensing a corresponding second top product from the second separation region, even when it contains significant proportions of hydrogen. Owing to the halving of the rectification column in the first separation region and the second separation region and the intermediately connected condenser-evaporator, the expansion chill which is formed in the expansion of the second proportion of the second tops gas is sufficient here for condensation. This is especially because lower volumes have to be condensed here owing to the preliminary separation that has been effected, as elucidated repeatedly.

It is particularly advantageous when the second proportion of the second tops gas, after the expansion to the lower pressure level and the heat exchange with the first proportion of the second tops gas, is compressed from the lower pressure level to a higher pressure level. For this compression, it is especially possible, as elucidated below, to use an arrangement composed of an expansion turbine with which the prior expansion of the second proportion of the second tops gas is conducted, and a turbocompressor in which the compression is effected. In this way, work released in the expansion can be recovered and a corresponding top product can simultaneously be compressed to a desired pressure. In other words, a turboexpander is thus advantageously used for expansion of the second proportion of the second tops gas to the lower pressure level in the context of the present invention, and a turbocompressor driven by the turboexpander is advantageously used for compression of the second tops gas from the lower pressure level to the higher pressure level.

Advantageously, within the context of the present invention, the lower pressure level is 6 to 11 bar and the higher pressure level is 10 to 15 bar. This enables provision of the cooling energy already mentioned for condensation of the first proportion of the second top product.

In the context of the present invention, it is advantageously the case that the second proportion of the second tops gas, after the expansion to the lower pressure level, after the heat exchange with the first proportion of the second tops gas, and before the compression from the lower pressure level to the higher pressure level, is subjected to heat exchange with the gas mixture which is at least partly fed into the first separation region as first separation feed in order to cool it. In this way, it is also possible to use cooling energy remaining after the use of the first proportion of the second tops gas for at least partial condensation of the first proportion of the second tops gas for cooling of the first separation feed.

As already mentioned, the condenser-evaporator, in the context of the present invention, can advantageously be cooled to an appropriate temperature level by means of ethylene coolant or by means of a fluid. The use of ethylene coolant from an ethylene cooling circuit is known in principle. Ethylene coolant can especially also be formed using fluids formed in a corresponding method. Ethylene coolant can also be used at points other than in the condenser-evaporator.

However, it can also be particularly advantageous when the condenser-evaporator is cooled using at least a portion of the first bottoms liquid, i.e. the bottoms liquid obtained in the first rectification. This predominantly comprises higher-boiling hydrocarbons than methane. These are predominantly hydrocarbons having two carbon atoms, i.e. ethane and ethylene. It can therefore be sufficient to use a corresponding bottoms liquid as coolant in a corresponding condenser-evaporator. This is especially true when a corresponding fluid is to be provided in the gaseous state and can therefore be at least partly evaporated in the condenser-evaporator.

In the context of the present invention, the first bottoms liquid, as mentioned, especially comprises higher-boiling hydrocarbons than methane that were previously present in the first separation feed or the gas mixture. The second tops gas, by contrast, comprises predominantly or exclusively hydrogen, methane and carbon dioxide which originate from the gas mixture or the first separation feed and have been transferred to the second separation region via the second separation feed. The first tops gas or the second separation feed has been enriched in corresponding light components and depleted of heavier components compared to the first separation feed.

The present invention also relates to a plant for obtaining one or more olefins, having means set up, using an oxidative coupling of methane, for forming a gas mixture comprising hydrogen, methane, carbon monoxide and higher-boiling hydrocarbons than methane and subjecting it to a low-temperature separation. According to the invention, a rectification column having a first separation region, a second separation region arranged above the first separation region, and a condenser-evaporator, especially arranged between the first separation region and the second separation region, has been provided for the low-temperature separation. Also provided in accordance with the invention have been means set up for cooling the gas mixture, for feeding it at least partly as first separation feed into the first separation region and for subjecting it to a first rectification in the first separation region to form a first tops gas and a first bottoms liquid. These means are also provided for forming a condensate using a first proportion of the first tops gas in the condenser-evaporator and for recycling it to the first separation region, for forming a second separation feed using a second proportion of the first tops gas and for feeding it into the second separation region, and for subjecting the second separation feed to a second rectification in the second separation region to form a second tops gas and a second bottoms liquid. As already mentioned, in a corresponding plant, it is advantageously possible for the first separation region and the second separation region to be disposed in a common outer shell.

With regard to features and advantages of a corresponding plant, reference is made explicitly to the method features elucidated above. This is also true of the plant envisaged advantageously, which has additionally been set up for performance of a method as elucidated above, and comprises the means set up for this purpose.

The invention is elucidated in detail in preferred configurations with reference to the appended drawings.

DETAILED DESCRIPTION OF THE DRAWING

Figure 1:
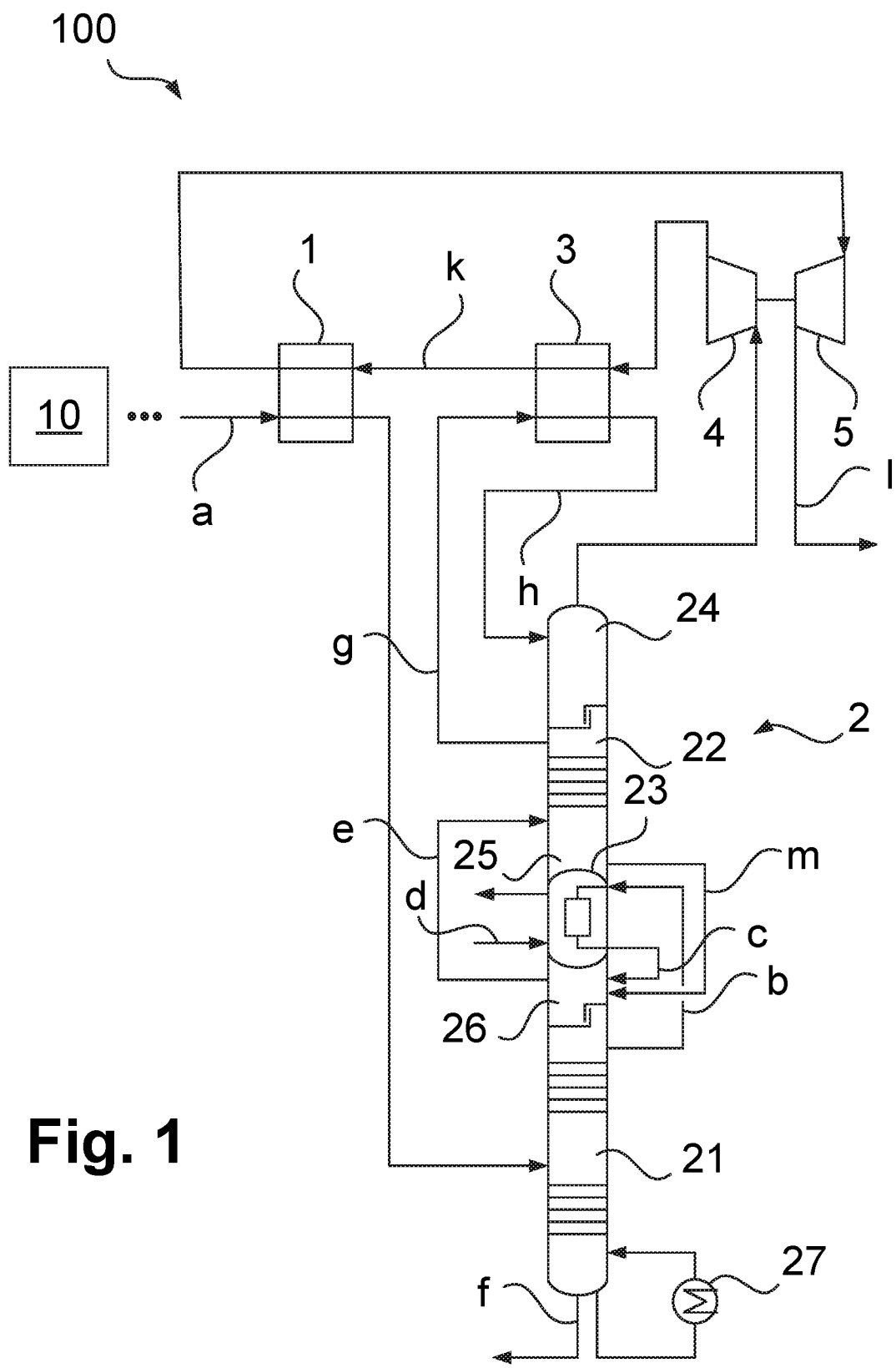
FIG. 1 illustrates a method in one embodiment of the invention in the form of a simplified process flow diagram.
Figure 2:
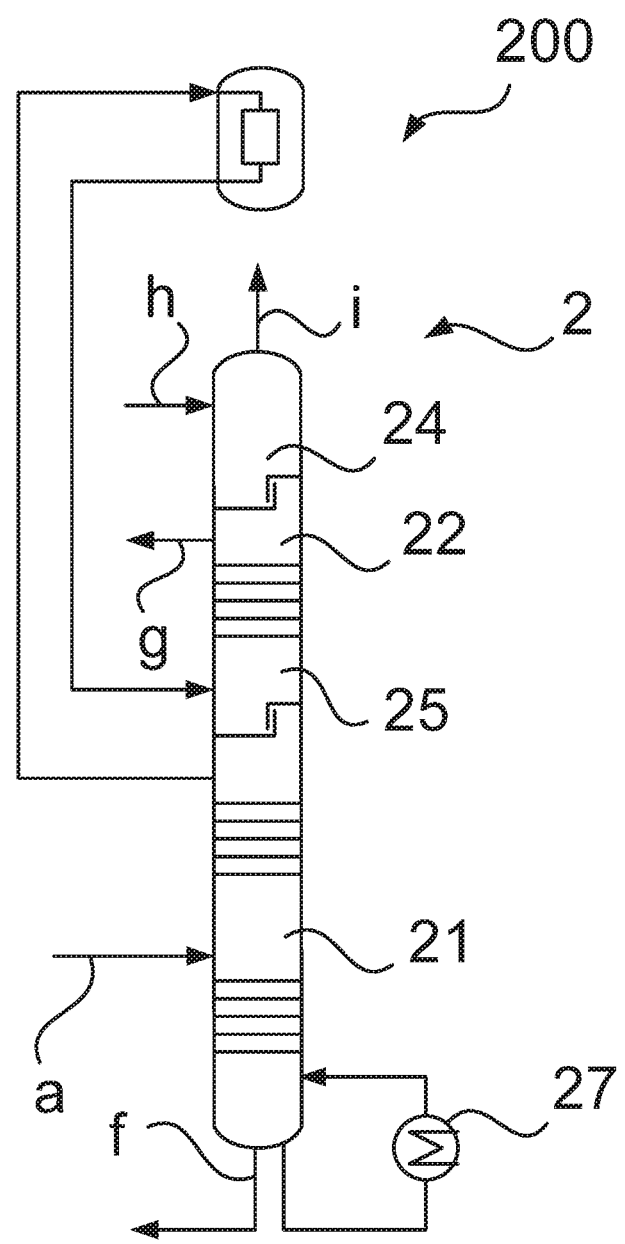
FIG. 2 illustrates an alternative of the method according to FIG. 1 in the form of a simplified process flow diagram in partial view.

FIGS. 1 and 2 illustrate methods according to embodiments of the invention in the form of greatly simplified process flow diagrams; FIG. 2 shows a partial view of an alternative method to the method according to FIG. 1, in which, however, the other components shown in FIG. 1 are used. The methods are respectively labelled 100 and 200 overall.

The components or method steps elucidated for FIGS. 1 and 2 are simultaneously part of a corresponding plant or are implemented in device form therein, and so the elucidations which follow also relate to corresponding plants. The diagram is greatly simplified especially in that devices that are provided in practice, such as regulators, valves, bypasses required for the startup of a corresponding plant, etc., are not illustrated. The person skilled in the art will envisage corresponding elements as required.

In the methods 100 and 200, an oxidative coupling of methane is used, as shown here in very simplified form and summarized by 10 in FIG. 1. There may be further methods or method steps assigned to or connected downstream of the oxidative coupling of methane 10, as elucidated by way of introduction and symbolized here by ellipses. The oxidative coupling of methane 10 can especially be fed with one or more methane-rich streams of matter, as is not shown here. The oxidative coupling of methane 10 may further be supplied with one or more oxygen-rich streams of matter, as is likewise not shown here. It is also possible, in particular, to recycle a methane-rich stream of matter formed in the methods 100 and 200 or downstream thereof into the oxidative coupling of methane 10. If a postcatalytic steamcracking elucidated at the outset is used, it may be supplied with one or more paraffin-rich streams of matter, for example one or more ethane or propane streams. These too can be formed in the methods 100 and 200 or downstream thereof, as also elucidated in detail hereinafter.

Using the oxidative coupling of methane 10, i.e. optionally also with use of further methods or method steps, especially for processing of a product mixture from the oxidative coupling of methane 10 and optionally the postcatalytic steamcracking, a gas mixture is provided, comprising not only methane but also lower-boiling components than methane, especially hydrogen and carbon monoxide, and higher-boiling hydrocarbons than methane, but barely any carbon dioxide or water, if any. Carbon dioxide and water have been removed upstream by suitable separation units.

A corresponding gas mixture, as illustrated here in the form of a stream of matter a, is first guided through a heat exchanger 1 and cooled therein. The correspondingly cooled gas mixture of the stream of matter a is fed into a rectification column 2 in the form of a separation feed, which is referred to here as "first" separation feed.

The rectification column 2 comprises, in the embodiments shown, a first separation region 21 and a second separation region 22. Corresponding separation regions are especially subdivided by separation plates, whereas other regions, namely empty spaces 24, 25 and 26, are not divided by corresponding separation plates. As well as the separation regions 21 and 22 and the empty spaces 24, 25 and 26, a condenser-evaporator 23 is provided, which is also arranged here in terms of construction between the separation regions 21 and 22 arranged one on top of another. An alternative arrangement is illustrated in FIG. 2.

In the first separation region 21 of the rectification column 2, the first separation feed, i.e. the fluid fed in in the form of stream of matter a, is subjected to a rectification, which is also referred to here to as "first" rectification. A bottoms liquid and a tops gas are formed, which are referred to here as "first" bottoms liquid and "first" tops gas. The first tops gas can be drawn off partly in gaseous form in the form of a stream of matter b, at least partly condensed in the condenser-evaporator 23 and fed into the empty space 26 as condensate in the form of a condensate stream c. A condensate that collects in the empty space 26 can be recycled to the first separation region via an overflow. A second proportion of the first tops gas can be discharged from the empty space 26 in the form of a stream of matter e and partly or completely fed into a lower region of the second separation region 22. A condensate in the form of a stream of matter m is transferred into the empty space 26 from a lower region of the second separation region 22 and can, like the condensate from the condenser-evaporator 23, flow away to the first separation region 21 via the overflow.

A rectification is conducted in the second separation region 22 of the rectification column 2, which is also referred to here as "second" rectification. A tops gas is formed therein, which is also referred to here as "second" tops gas. A first proportion of this can be drawn off in the form of a stream of matter g, at least partly liquefied or condensed in a heat exchanger 3, and recycled in the form of a stream of matter h into an empty space 24 of the rectification column 2. Condensate that collects in the empty space 24 can be recycled to the second separation region 22 via an overflow.

A second proportion of the second tops gas, i.e. of the tops gas from the second separation region 22, can be drawn off from the empty space 24 in gaseous form and fed in the form of a stream of matter i to an expansion in an expansion turbine 4. The expansion in the expansion turbine 4 reduces the temperature of the stream of matter i, which is now illustrated by k. In the heat exchanger 3, the stream of matter i or k can be subjected to heat exchange with the first proportion of the second tops gas from the second separation region 22, which is guided through the heat exchanger 3 in the form of the stream of matter g. In this way, the present invention enables condensation of the corresponding tops gas component. After the heat exchange in the heat exchanger 3, a corresponding stream of matter k can be guided through the heat exchanger 1 and can cool down the stream of matter a here. Subsequently, the stream of matter k can be recompressed in a turbocompressor 5 which can be driven by the turboexpander 4 and discharged from the method in the form of a stream of matter I.

The rectification column 2 can be operated using a reboiler 27. The bottoms liquid from the first separation region 21 can be drawn off at least partly in the form of a stream of matter f, which, as mentioned, comprises essentially hydrocarbons having two or more carbon atoms.

In the method 100 illustrated in FIG. 1, the condenser-evaporator 23 is cooled using an ethylene coolant stream d which is evaporated in an evaporation space of the condenser-evaporator 23. However, the condenser-evaporator 23 can also, as is not illustrated here, be cooled using the stream of matter f, i.e. the first bottoms liquid from the first separation region 21 of the rectification column 2. This stream of matter f too is evaporated and discharged from the method in evaporated form.

FIG. 2 illustrates an alternative of the method according to FIG. 1 in the form of a simplified process flow diagram in partial view. Only the rectification column 2 is shown. Its incorporation into the method 200 is apparent from the labelling of the fluid streams.

This alternative corresponds to a particularly advantageous configuration of the method according to the invention, because the separation regions 21 and 22 which can be operated at a comparable pressure level can be arranged here within a common outer shell, but not the condenser-evaporator 23 in which, for example, low-pressure ethylene coolant is used. In this way, it is also possible, for example, to use a smaller vessel diameter for the condenser-evaporator 23. Alternatively, the condenser-evaporator can also be disposed in the free volume of the second separation region 22.

The efflux of liquid from the second separation region 22 to the first separation region is accomplished here by means of an overflow. As an alternative, a regime analogous to stream m according to FIG. 1 is also possible.

The invention claimed is:

1. Method (100, 200) of obtaining one or more olefins, in which, using an oxidative coupling of methane (10), a gas mixture comprising hydrogen, methane, carbon monoxide and higher-boiling hydrocarbons than methane is formed and is subjected to a low-temperature separation (1-5), characterized in that the low-temperature separation (1-5) is conducted using a rectification column (2) having a first separation region (21), a second separation region (22) arranged above the first separation region (21), and a condenser-evaporator (23), wherein the gas mixture is cooled, fed at least partly as first separation feed into the first separation region (21) and subjected to a first rectification in the first separation region (21) to form a first tops gas and a first bottoms liquid, wherein, using a first proportion of the first tops gas in the condenser-evaporator (23), a condensate which is recycled to the first separation region and, using a second proportion of the tops gas, a second separation feed which is fed into the second separation region (22) are formed, and wherein the second separation feed is subjected to a second rectification in the second separation region (22) to form a second tops gas and a second bottoms liquid.

2. Method (100, 200) according to claim 1, in which the cooling of the gas mixture prior to the at least partial feeding as first separation feed into the first separation region (21) is effected to a temperature level of −70 to −95° C.

3. Method (100, 200) according to claim 1, in which one pressure level at which the rectification column (2) is operated is 24 to 36 bar.

4. Method (100, 200) according to claim 1, in which, using a first proportion of the second tops gas, a condensate which is recycled to the first separation region is formed, wherein a second proportion of the second tops gas is expanded to a lower pressure level and subjected to a heat exchange with the first proportion of the second tops gas.

5. Method (100, 200) according to claim 4, in which the second proportion of the second tops gas, after the expansion to the lower pressure level and the heat exchange with the first proportion of the second tops gas, is compressed from the lower pressure level to a higher pressure level.

6. Method (100, 200) according to claim 5, in which a turboexpander (4) is used for expansion of the second proportion of the second tops gas to the lower pressure level, and a turbocompressor (5) driven by the turboexpander (4) is used for compression of the second tops gas from the lower pressure level to the higher pressure level.

7. Method according to claim 5, in which the lower pressure level is 6 to 11 bar and the higher pressure level is 10 to 15 bar.

8. Method according to claim 5, in which the second proportion of the second tops gas, after the expansion to the lower pressure level, after the heat exchange with the first proportion of the second tops gas, and before the compression from the lower pressure level to the higher pressure level, is subjected to heat exchange with the gas mixture which is at least partly fed into the first separation region (21) as first separation feed in order to cool it.

9. Method according to claim 1, in which the condenser-evaporator (23) is cooled by means of ethylene coolant.

10. Method according to claim 1, in which the condenser-evaporator (23) is cooled using at least a portion of the first bottoms liquid.

11. Plant for obtaining one or more olefins, having means set up, using an oxidative coupling of methane (10), for forming a gas mixture comprising hydrogen, methane, carbon monoxide and higher-boiling hydrocarbons than methane and subjecting it to a low-temperature separation (1-5), characterized in that a rectification column (2) having a first separation region (21), a second separation region (22) arranged above the first separation region (21), and a condenser-evaporator (23) is provided for the low-temperature separation (1-5), wherein means set up for cooling the gas mixture, for feeding it at least partly as first separation feed into the first separation region (21) and for subjecting it to a first rectification in the first separation region (21) to form a first tops gas and a first bottoms liquid, for forming a condensate using a first proportion of the first tops gas in the condenser-evaporator (23) and for recycling it to the first separation region, for forming a second separation feed using a second proportion of the first tops gas and for feeding it into the second separation region (22), and for subjecting the second separation feed to a second rectification in the second separation region to form a second tops gas and a second bottoms liquid are provided.

12. Plant according to claim 11, in which the first separation region (21), the second separation region (22) and the condenser-evaporator (23) are disposed in a common outer shell.

13. Plant according to claim 11, set up to conduct a method of obtaining one or more olefins, in which, using an oxidative coupling of methane (10), a gas mixture comprising hydrogen, methane, carbon monoxide and higher-boiling hydrocarbons than methane is formed and is subjected to a low-temperature separation (1-5), characterized in that the low-temperature separation (1-5) is conducted using a rectification column (2) having a first separation region (21), a second separation region (22) arranged above the first separation region (21), and a condenser-evaporator (23), wherein the gas mixture is cooled, fed at least partly as first separation feed into the first separation region (21) and subjected to a first rectification in the first separation region (21) to form a first tops gas and a first bottoms liquid, wherein, using a first proportion of the first tops gas in the condenser-evaporator (23), a condensate which is recycled to the first separation region and, using a second proportion of the tops gas, a second separation feed which is fed into the second separation region (22) are formed, and wherein the second separation feed is subjected to a second rectification in the second separation region (22) to form a second tops gas and a second bottoms liquid.

14. Method (100, 200) according to claim 2, in which one pressure level at which the rectification column (2) is operated is 24 to 36 bar.

15. Method (100, 200) according to claim 2, in which, using a first proportion of the second tops gas, a condensate which is recycled to the first separation region is formed, wherein a second proportion of the second tops gas is expanded to a lower pressure level and subjected to a heat exchange with the first proportion of the second tops gas.

16. Method (100, 200) according to claim 3, in which, using a first proportion of the second tops gas, a condensate which is recycled to the first separation region is formed, wherein a second proportion of the second tops gas is expanded to a lower pressure level and subjected to a heat exchange with the first proportion of the second tops gas.

17. Method according to claim 6, in which the lower pressure level is 6 to 11 bar and the higher pressure level is 10 to 15 bar.

18. Method according to claim 6, in which the second proportion of the second tops gas, after the expansion to the lower pressure level, after the heat exchange with the first proportion of the second tops gas, and before the compression from the lower pressure level to the higher pressure level, is subjected to heat exchange with the gas mixture which is at least partly fed into the first separation region (21) as first separation feed in order to cool it.

19. Method according to claim 7, in which the second proportion of the second tops gas, after the expansion to the lower pressure level, after the heat exchange with the first proportion of the second tops gas, and before the compression from the lower pressure level to the higher pressure level, is subjected to heat exchange with the gas mixture which is at least partly fed into the first separation region (21) as first separation feed in order to cool it.

20. Method according to claim 2, in which the condenser-evaporator (23) is cooled by means of ethylene coolant.

* * * * *